(12) United States Patent
Hoenes (10) Patent No.: US 8,231,548 B2
(45) Date of Patent: Jul. 31, 2012

(54) PORTABLE MEASURING SYSTEM HAVING A MOISTURE-PROOF ASSEMBLY SPACE

(75) Inventor: Joachim Hoenes, Zwingenberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 521 days.

(21) Appl. No.: 12/355,784

(22) Filed: Jan. 18, 2009

(65) Prior Publication Data

US 2009/0182244 A1   Jul. 16, 2009

Related U.S. Application Data

(63) Continuation of application No. PCT/EP2007/057023, filed on Jul. 10, 2007.

(30) Foreign Application Priority Data

Jul. 18, 2006 (EP) .................................... 06117422

(51) Int. Cl.
*A61B 5/00* (2006.01)
(52) U.S. Cl. ....................................... 600/583; 600/573
(58) Field of Classification Search .................. 600/573, 600/583; 606/181
See application file for complete search history.

(56) References Cited

U.S. PATENT DOCUMENTS

| | | | |
|---|---|---|---|
| 4,911,344 A | 3/1990 | Kahler | |
| 5,286,362 A | 2/1994 | Hoenes et al. | |
| 5,489,414 A | 2/1996 | Schreiber et al. | |
| 5,505,308 A | 4/1996 | Eikmeier et al. | |
| 6,093,156 A | 7/2000 | Cunningham et al. | |
| 6,908,008 B2 | 6/2005 | Pugh | |
| 2002/0052618 A1 | 5/2002 | Haar et al. | |
| 2002/0170823 A1 | 11/2002 | Housefield et al. | |
| 2003/0116583 A1 | 6/2003 | Pugh | |
| 2004/0092842 A1 | 5/2004 | Boecker et al. | |
| 2005/0015020 A1* | 1/2005 | LeVaughn et al. | 600/583 |
| 2005/0033196 A1* | 2/2005 | Alroy | 600/573 |
| 2006/0094986 A1* | 5/2006 | Neel et al. | 600/583 |
| 2006/0173380 A1 | 8/2006 | Hoenes et al. | |
| 2006/0271083 A1* | 11/2006 | Boecker et al. | 606/181 |
| 2008/0180652 A1 | 7/2008 | Petrich et al. | |

FOREIGN PATENT DOCUMENTS

DE  103 32 488 A1  2/2005

(Continued)

OTHER PUBLICATIONS

International Preliminary Report on Patentability dated Feb. 19, 2009.

*Primary Examiner* — Max Hindenburg
*Assistant Examiner* — Charles Becker
(74) *Attorney, Agent, or Firm* — Bose McKinney & Evans LLP (57) ABSTRACT

A portable measuring system which analyzes a liquid sample for at least one analyte. The portable measuring system has a substantially moisture-proof housing with an internal atmosphere. The housing prevents moisture from the air and water vapor from penetrating into the housing. The portable measuring system also has at least one test element support inserted into the internal atmosphere of the housing. The test element support is equipped with a retaining structure and a test element that is supported by the retaining structure. The test element support is designed such that, after insertion into the internal atmosphere, the test element is exposed to the internal atmosphere. A release mechanism is also provided which can convey at least one test element into an application position within the internal atmosphere of the housing. In this application position, the liquid sample can be applied to the test element.

23 Claims, 2 Drawing Sheets

FOREIGN PATENT DOCUMENTS

| | | |
|---|---|---|
| EP | 0 640 393 B1 | 3/1995 |
| EP | 1 203 563 A2 | 5/2002 |
| EP | 1 488 736 A1 | 12/2004 |
| EP | 1 637 078 A1 | 3/2006 |
| WO | WO 01/48461 A1 | 7/2001 |
| WO | WO 02/18940 A2 | 3/2002 |
| WO | WO 02/18940 A3 | 3/2002 |
| WO | WO 02/055008 A2 | 7/2002 |
| WO | WO 03/083469 A2 | 10/2003 |
| WO | WO 2006/047135 A1 | 5/2006 |

* cited by examiner

PORTABLE MEASURING SYSTEM HAVING A MOISTURE-PROOF ASSEMBLY SPACE

This application is a continuation application of International Application PCT/EP2007/057023, filed Jul. 10, 2007, which claims priority to EP 06117422.3, filed Jul. 18, 2006, which are hereby incorporated by reference in their entirety.

BACKGROUND

The invention relates to a portable measuring system with a small assembly space that can be used to analyze a liquid sample for at least one analyte contained therein. Measuring systems of this kind are used in particular in the field of medicine, for example, for blood glucose monitoring, or in the field of chemical or biological analysis, for example, environmental analysis.

Monitoring of blood glucose concentration is an essential part of the daily routine of diabetics. Blood glucose concentration must be determined quickly and reliably several times a day in order, if appropriate, to be able to take suitable medical measures. So as not to restrict the diabetic's daily routine any more than is necessary, suitable portable devices are often employed which are intended to be easy to carry and to operate such that the blood glucose concentration can be measured, for example, at the workplace or even during leisure time.

Various portable devices are presently available on the market, some of them functioning according to different measurement methods. Various diagnostic methods are used in these devices, for example, optical or even electrochemical measurement methods. An example of a frequently employed measurement method utilizes a special kind of electrochemical test strips. These test strips are, for example, configured such that a predetermined quantity of blood is conveyed to an electrode system via a capillary system on the test strip. For modem test strips, a quantity of blood of ca. 1.5 ml is sufficient, sometimes even quantities of blood of less than 1 ml can be used. The electrode system may, for example, involve gold electrodes that are provided with a coating. The coating in most cases contains different enzymes and so-called mediators and has the effect that charge carriers (for example in the form of redox molecules) form within the sample on the electrodes, the concentration of these charge carriers being dependent on the blood glucose concentration. The concentration of these charge carriers can be determined by means of the gold electrodes and a suitable measurement system, for example, by means of a current-voltage measurement, and from this concentration it is possible, finally, to calculate the blood glucose concentration. An example of electrochemical test strips of this kind is set out in U.S. Pat. No. 5,286,362.

As an alternative to the electrochemical measurement method described above, other measurement principles can also be used. Thus, for example, Publication No. WO 01/48461 describes a test strip with light guides for examining a sample, in particular, of a body fluid, in which a reagent system, upon reaction with the sample, leads to a characteristic and optically measurable change in a detection zone. By way of light guides that are let into the test strip, this change can be evaluated by an evaluation device.

The test strips thus form an important element of portable diagnostic systems. Typically, about 5 to 7 of such test strips are needed each day by a diabetic. It is essential that the test strips are stored in a clean and dry condition to ensure that the measurement of the blood glucose concentration is not rendered inaccurate by contamination or by the effect of moisture.

For this purpose, the test strips are usually stored in suitable containers in order to then be removed by the user from the test strip container for a measurement and fitted into a corresponding measuring device. Such measuring devices, for example, measuring devices for electrochemical or optical determination of the blood glucose concentration, are known to persons skilled in the art and described, for example, in US Patent Publication No. 2002/0170823 A1.

For storing and dispensing the test strips, magazine systems are also known. For example, US Patent Publication No. 2003/0116583 A1, EP 0 640 393 and U.S. Pat. No. 4,911,344 describe suitable storage systems in which several test strips are stored in a magazine. EP 1 488 736 also describes a system which contains, instead of individual test strips, a tape cassette composed of a long individual test strip with a plurality of test fields.

In addition to systems in which the test strip magazine and measuring device are used as separate units, integrated systems also exist which not only comprise several test strips stored in one magazine, but also afford the possibility of evaluation of these test strips. Examples of systems of this kind are to be found in U.S. Pat. Nos. 5,489,414, 6,093,156, and Publication Nos. WO 02/18940, WO 02/055008 or WO 03/083469. Some of these systems, for example the system described in U.S. Pat. No. 6,093,156 or Publication No. WO 03/083469, already comprise an integrated lancet system too, which makes it possible to perforate the skin to generate a blood droplet and then permits analysis of the blood droplet using one and the same measuring system.

However, in the systems known from the prior art, the problem surrounding moisture sensitivity, of the test strips has only been partially solved. Thus, for example, German Patent No. DE 103 32 488 and US Patent Publication No. 2005/0033196 each disclose test systems with integrated lancet system and test strips, in which blood droplets are applied directly to test strips. In these cases, however, the test strips are largely unprotected and thus exposed to the air moisture.

Air moisture, especially at elevated temperatures and over long periods of time, can affect the sensitivity of the test strips and thus render the measurement inaccurate. To avoid this, the systems disclosed in Publication Nos. WO 03/083469 or WO 02/055008, for example, contains separate, exchangeable, airtight test strip magazines, which are inserted into the actual measuring device. However, this requires dual packaging of the test strips, which requires considerable assembly space, since the test strips are now surrounded by the actual magazine wall as primary packaging and in addition by the wall of the measuring device. Analogously, Publication No. WO 2006/047135 also describes a complex test strip dispenser with a test strip "cartridge." Here, a device housing encloses a magazine (cartridge), which for its part has an outer envelope and an inner envelope. The test strips are stored in a moisture-proof manner in the magazine. Since optimization of size is a crucial factor for portable medical measuring devices, the disadvantage of the dual packaging of the systems known from the prior art is in some cases critically important when it comes to the patient's acceptance of the measuring device.

Other systems, for example, the system disclosed in U.S. Pat. No. 5,489,414, are based on individually sealed test elements. These test elements can be designed, for example, as multi-use test elements with individually sealed test areas. A disadvantage of these, however, is that the seal of the test elements has to be removed before use, which requires additional mechanical action, for example, or manual action on the part of the patient. Automatic removal of the seal, for example by perforation of the seal, requires additional mechanical elements and drive elements inside the measuring device, which in turn greatly increases the assembly space and/or the energy requirement of the systems.

These examples show that it has not hitherto been possible to entirely solve the problems of, on the one hand, ensuring that disposable test elements for reloading of the measuring devices can be transported to the measuring device in an airtight package or seal (for example commercially) and, on the other hand, of ensuring that these sealed test elements can then be used in the measuring device itself with removal of the seal.

SUMMARY OF THE INVENTION

Embodiments according to the present invention provide a portable measuring system for analysis of a liquid sample, in particular, for use in medicine, which system has a small assembly space and yet permits substantially airtight storage of test elements in the measuring device.

A portable measuring system is disclosed which is used to analyze a liquid sample for at least one analyte contained therein. The portable measuring system can, in particular, be a system for glucose measurement, in particular, blood glucose measurement, and/or for cholesterol measurement and/or coagulation measurement. Alternatively, or in addition, however, other analytes can also be determined, for example, for their concentration or presence, or corresponding other analyses can be performed, for example, pH measurements or similar chemical analyses. It is also possible, for example, to perform immunology measurements or similar measurements using the test device. The sample will in particular be a liquid sample, for example, blood, urine, saliva or stools. However, other kinds of samples are also conceivable, for example gaseous samples.

The analysis is based on the use of test elements, for example, optical and/or electrochemical test elements, as are known from the prior art. For example, these test elements can be in the form of test strips.

The portable measuring system comprises a measuring device that has a moisture-proof housing with an internal atmosphere. The moisture-proof housing prevents air moisture and/or water vapor (collectively referred to as "moisture") from penetrating into the internal atmosphere of the housing when the moisture-proof housing is in its closed state. This can be achieved, for example, by suitable sealing elements and/or production methods known from the prior art.

The portable measuring system also has at least one test element support which can be inserted into the internal atmosphere of the housing and which has at least one retaining structure and at least one test element that is supported by the at least one retaining structure and that is used to analyze the liquid sample. The at least one test element support is designed in such a way that, after insertion of the test element support into the internal atmosphere of the housing, the at least one test element is exposed to said internal atmosphere.

To this extent, the proposed system has similarities to the magazine system disclosed in U.S. Pat. No. 6,908,008, for example. In contrast to the system known from U.S. Pat. No. 6,908,008, in which a test strip has to be dispensed from the airtight magazine for application of the liquid sample, an underlying concept of embodiments taught herein is that the liquid sample can be applied to a test element to be used within the internal atmosphere of the housing itself.

For this purpose, the disclosed portable measuring system can have a release mechanism designed to convey at least one test element into an application position within the internal atmosphere of the housing. The liquid sample can be applied to the at least one test element in the application position.

The disclosed portable measuring system therefore does not need an airtight primary packaging around the test elements, which packaging would have to be removed prior to application of the liquid sample, or from which packaging the test elements would have to be withdrawn prior to application of the liquid sample. In this way, the assembly space of the portable measuring system can be considerably reduced.

The at least one test element support can be sold and stored in a removable package, for example, in what is referred to as a "blister pack." In this package, the test elements are protected against moisture from ambient air and other atmospheric influences. To use them, the patient opens the package and inserts the test element support into the internal atmosphere of the housing, for which purpose the moisture-proof housing can be flipped open, pushed open or unscrewed, for example. Only during this brief insertion time are the test elements exposed to the ambient air. Then, after the housing has been closed, the test elements are stored directly in the internal atmosphere of the housing without any additional sealing. The outward seal is now effected by the measuring device itself. For this purpose, all or part of the housing of the measuring device is designed to be moisture-proof, in such a way that the internal atmosphere of the housing is protected.

In addition, a desiccant can be received in the internal atmosphere of the housing. Alternatively, or in addition, a desiccant can also be connected to the at least one test element support, such that a new, unused desiccant is inserted into the internal atmosphere of the housing each time a test element support is replaced. The amount of desiccant is preferably to be chosen such that the desiccant is able to bind the moisture that penetrates through the housing walls by diffusion and by passing through microscopic leaks during the desired storage period, and preferably, in addition, the moisture that is introduced when applying the sample into the internal atmosphere of the housing.

The possibility of air moisture penetrating into the internal atmosphere of the housing exists only for the brief time in which the liquid sample is being applied to the at least one test element to be used. For application of the liquid sample, the housing has an application opening. This application opening is equipped with at least one sealing element. This at least one sealing element can have a sealing lip, a sealing slide, an application flap, a movable sealing element and/or a two-component plastic structure with at least one rigid and at least one flexible housing component. This application opening and the at least one sealing element connected thereto are in principle required only once per measurement system, such that assembly space can be cut down and no complicated sealing constructions for several openings are needed.

The liquid sample can be applied, for example, by a procedure in which a patient, for example, using a lancet system, generates a blood droplet on the skin surface, for example, of a finger pad, and then opens the application opening by pressing or sliding it with the finger pad or with another finger. In this way, the blood droplet can then be applied to the at least one test element within the internal atmosphere of the housing.

After the measurement, the sample on the test element is dried by the dry environment within the internal atmosphere of the housing. For this purpose, it is possible (see above) to provide a suitable excess of desiccant. For example, in order to dry a liquid sample, an amount of approximately 10 mg of a desiccant with a capacity of approximately 10% by weight is usually required for every 1 microliter of sample volume.

To improve the sealing function of the at least one sealing element, a pressure-equalizing structure can also be provided in the portable measuring system. This pressure-equalizing structure prevents penetration of water vapor and/or moisture when a pressure of the internal atmosphere of the housing changes relative to the air pressure outside the internal atmosphere of the housing. Such pressure fluctuations occur, for example, upon cooling or heating of the portable measuring system, which processes are associated with a change in the volume of the air in the internal atmosphere of the housing and thus with a pressure fluctuation. This pressure-equalizing structure can, for example, comprise a flexible volume-modifying element, in particular a pressure-equalizing membrane. Other possibilities are also conceivable.

To monitor the internal atmosphere of the housing, a moisture sensor and/or a temperature sensor can also be provided. The moisture sensor measures the moisture in the internal atmosphere of the housing, and the temperature sensor measures the temperature. In this way, for example, a warning system can emit a warning to a user if the moisture in the internal atmosphere of the housing and/or the temperature of the internal atmosphere of the housing exceeds a predefined threshold value (or in each case one or more threshold values). Other types of measurements are also conceivable, for example, monitoring a "total dose" (for example, a time integral of the moisture and temperature) to which the test elements have thus far been subjected in the internal atmosphere of the housing such that, for example when they have been subjected to a maximum extent, a warning can be generated to tell the user that new test elements ought to be used. It is thus possible, for example, to monitor a "climate integrator", which represents a time integral over temperature and moisture, for example, and accordingly to generate a warning when a threshold value is exceeded.

The at least one retaining structure can be designed in various ways. For example, it can be a drum with peripheral receiving slits for strip-shaped test elements. This drum can be a simple injection-molded part, for example. Test element tapes with a plurality of measurement areas can also be used, in which case, for example, an unwinding mechanism can be provided. Moreover, the at least one retaining structure can have, for example, at least one retaining rotor that is able to rotate in the moisture-proof housing.

The portable measuring system can also have an electronic evaluation device for determining the presence and/or concentration of the at least one analyte. This electronic evaluation device is in this case preferably adapted to the nature and function of the at least one test element. Thus, for example, an evaluation device can be provided for electrochemical measurements by means of electrochemical test elements. Alternatively, or in addition, an optical evaluation is also conceivable.

The at least one test element may have at least one reagent layer, which is designed to change at least one property, in particular, an optical and/or electro-chemical property, upon contact with the at least one analyte to be detected. With the test element support inserted into the internal atmosphere of the housing, the at least one reagent layer of each test element is preferably exposed directly to the internal atmosphere of the housing. "Directly" can also be understood as meaning a connection of the reagent layer to the internal atmosphere of the housing via a capillary. In contrast to the prior art, for example, U.S. Pat. No. 5,489,414, individual sealing of the test elements is not required.

The portable measuring system as such maybe provided with at least one integrated lancet system for perforating an area of skin. This integrated lancet system can be preferably received in the moisture-proof housing. It is thus possible to first carry out a perforation procedure via the application opening and immediately thereafter, i.e., without changing the position of the area of skin to be perforated, to generate a blood droplet, with subsequent direct application of this blood droplet to a test element. This minimizes the number of times the housing is opened and during which moisture from ambient air could penetrate into the internal atmosphere of the housing. Moreover, as discussed above, only a single application opening is needed in principle. In this way, the assembly space of the proposed portable measuring system can be made very small. Such a construction can be achieved only with difficulty when using the magazine solutions known from the prior art or the systems in which the test elements are sealed individually. The integrated lancet system can have a plurality of disposable lancets, for example, such that a fresh, unused lancet can be used for each perforation.

Further details and features of the invention will become clear from the following description of illustrative embodiments. The respective features can be embodied either singly or in several combinations with one another, though the invention is not limited to the illustrative embodiments.

BRIEF DESCRIPTION OF DRAWINGS

The above-mentioned aspects of the present invention and the manner of obtaining them will become more apparent and the invention itself will be better understood by reference to the following description of the embodiments of the invention, taken in conjunction with the accompanying drawings, wherein.

The illustrative embodiments are shown schematically in the figures. Identical reference numbers in the individual figures designate elements which are identical or whose functions are identical, or which correspond to one another in terms of their function.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
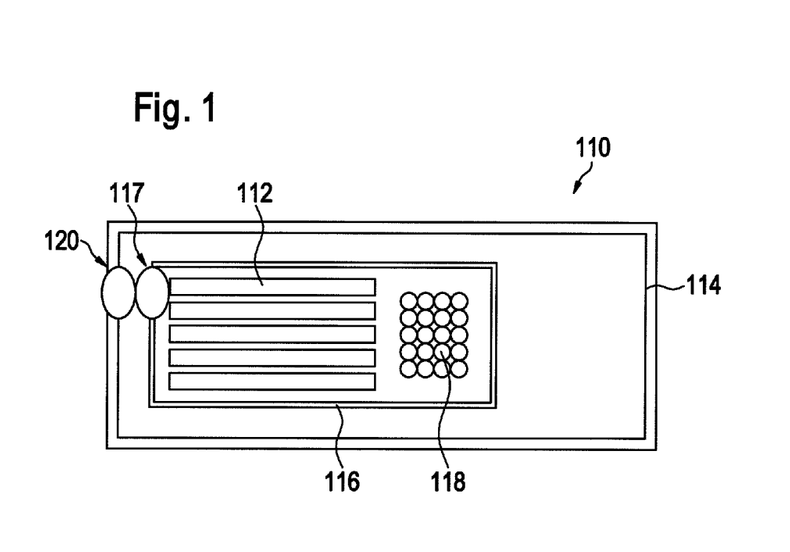
FIG. 1 shows a portable measuring system corresponding to the prior art, with dual enclosure of test elements.

FIG. 1 is a schematic representation of a portable measuring system 110 corresponding to, for example, the system disclosed in U.S. Pat. No. 6,908,008. In this case, the portable measuring system 110 is designed as a simple storing and dispensing system (dispenser) for test elements 112 in the form of test strips. An electronic evaluation device is not provided in this example.

The portable measuring system 110 in FIG. 1 has a housing 114 which, in this example, is not necessarily designed to be moisture-proof. Instead, the test elements 112 are stored in a moisture-proof primary packaging 116. Moreover, a desiccant 118 is also accommodated in this primary packaging 116. Such desiccants are known to persons skilled in the art.

For example, these desiccants can be silica gel, a molecular sieve and/or other chemicals that absorb air moisture.

To use the portable measuring system according to FIG. 1, the primary packaging 116 is inserted into the housing 114. A test element 112 can be dispensed through a dispensing opening 117 of the primary packaging 116 and through an opening 120 of the housing 114 by means of a dispensing mechanism (not shown here). To prevent air moisture from penetrating into the primary packaging 116 during this dispensing procedure, an individual seal (for example a sealing film) of the test element 112 can be punctured during the dispensing procedure. Other configurations are also known, for example closable dispensing slits or the like in the area of the dispensing opening 117.

A disadvantage of the known portable measuring system 110 according to FIG. 1 is, as has been explained above, the assembly space needed for the dual packaging of the test elements 112.

Figure 2:
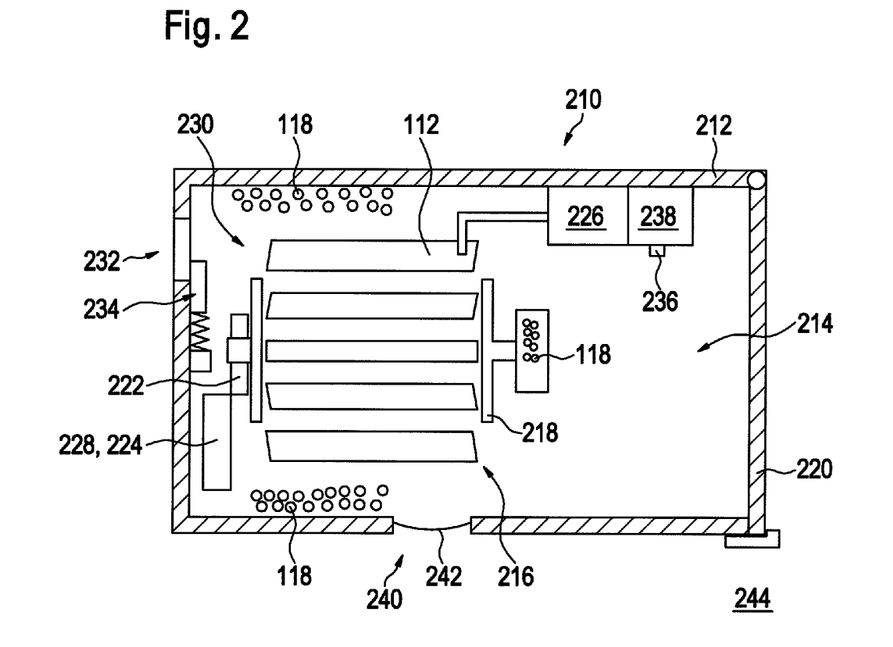
FIG. 2 shows a portable measuring system according to the present invention without primary packaging of the test elements.

In contrast to the device according to FIG. 1, a first illustrative embodiment of a portable measuring system 210 according to the invention is shown in FIG. 2. In this illustrative embodiment, it is assumed that the portable measuring system 210 is used to determine blood glucose concentrations. As has been explained above, however, other possible uses are also conceivable. For this purpose, the portable measuring system 210 in this example has a moisture-proof housing 212, which encloses an internal atmosphere 214 of the housing.

The "internal atmosphere of the housing" designates the cavity enclosed by the moisture-proof housing 212 and at the same time also the atmosphere, that is to say the properties of the gas (generally air) in the cavity. In the simplified depiction according to FIG. 2, the moisture-proof housing 212 has a single cavity, although other configurations are also conceivable. For example, it is not absolutely necessary for the whole of the moisture-proof housing to be moisture-proof as such. All that is required is that the moisture-proof housing 212 encloses in a moisture-proof manner the area in which test elements 112 are received (internal atmosphere 214 of the housing).

"Moisture-proof" is understood here not only as protection against splash water or rain, but also protection against water vapor and air moisture. Complete watertightness can also be provided. It should be noted, however, that one hundred percent protection against air moisture is in most cases not technically feasible, with the result that "moisture-proof" or "substantially moisture-proof" is also to be understood as meaning that penetration of air moisture is merely delayed. The moisture penetrating through the walls of the housing 114 as a result of diffusion is bound by the desiccant 118. For example, with penetration of 1 mg of air moisture per day, a supply of desiccant 118 of 1 g with 10% by weight binding capacity ensures a storage period of about 100 days.

The portable measuring system according to the illustrative embodiment in FIG. 1 is based on measurement by means of test elements 112, which can be designed according to the prior art. For example, these can be electrochemical test strips, for example, capillary-gap test elements and/or optical test strips.

The test elements 112 are held on a test element support 216 which can be inserted into the internal atmosphere 214 of the housing and which in turn has a retaining structure 218. This retaining structure 218 can, as in FIG. 2, be designed in the form of a drum, for example, on which the test elements 112 are received peripherally in radial longitudinal slits. In contrast to FIG. 1, a primary packaging 116 is not used, which means that the test elements 112 are exposed directly to the internal atmosphere 214 of the housing. The substantially moisture-proof housing 212 thus replaces the primary packaging 116 and so takes over the functions of the elements 114 and 116 according to FIG. 1.

The test element support 216 can be removed from the moisture-proof housing 212 via an insertion opening 220, closable in a moisture-proof manner (for example a lockable flap sealed off by an O-ring), and can be replaced by a test element support 216 which is equipped with unused test elements 112 and which, for this purpose, is taken from a blister pack, for example. When inserted, the test element support 216 engages in a receiving seat 222, in which it is mounted so as to rotate by means of a drive 224.

A desiccant 118 is also received in the internal atmosphere of the housing. Alternatively, or in addition, a desiccant 118 can be received on and/or in the test element support 216 such that this desiccant 118 is also renewed each time a test element support 216 is replaced.

In this example, the drive 224 acts as a release mechanism 228, by means of which a test element 112 to be used is conveyed into an application position 230. In this application position 230, a liquid sample can be applied to the test element 112 in the moisture-proof housing 212 via an application opening 232. For this purpose, the application opening 232 has a sealing element 234. In this illustrative embodiment, this sealing element 234 according to FIG. 2 is designed as a sealing slide which can be pushed aside, for example by a patient's finger, such that the application opening 232 is freed. A blood droplet present on the finger can then be applied to the test element 112 to be used in the application position 230. For this purpose, the test element 112 to be used can also be pushed by a mechanism (not shown here) nearer to the application opening 232.

In the illustrative embodiment according to FIG. 2, it is assumed herein below that the test elements 112 are electrochemical test elements, for example, test elements in the form of capillary gap test elements. Accordingly, an electronic evaluation device 226 is provided which electrically contacts the test element 112 located in the application position 230 and generates a corresponding measured value. For this purpose, the electronic evaluation device 226 can comprise, for example, a microcomputer, evaluation electronics, operating elements (e.g., pushbuttons, switches, keys, etc.), acoustic and/or optical output elements (e.g. one or more displays), data memories and other elements. Electronic evaluation devices 226 of this kind are known from the prior art. The electronic evaluation device 226 can, for example, also control the release mechanism 228.

Moreover, in the illustrative embodiment according to FIG. 2, a moisture sensor 236 (it can alternatively or additionally be a temperature sensor) and a warning system 238 are provided in the internal atmosphere 214 of the housing. For example, the warning system 238 can be a component part of the electronic evaluation device 226. The warning system can be designed, for example, in such a way that it emits an acoustic and/or optical warning to a user as soon as the air moisture in the internal atmosphere 214 of the housing exceeds a predetermined threshold value. As has been described above, another mode of operation is also conceivable, for example, an integration of the air moisture over time. This can also be done taking into account a measured temperature in the internal atmosphere 214 of the housing.

The moisture-proof housing 214 is designed, for example, as a one-part or multi-part injection molded component. Methods for making injection-molded housings of this kind moisture-proof are known to persons skilled in the art. For this purpose, suitable plastics with low permeability for air moisture and oxygen and/or suitable sealing devices (e.g. sealing rings) can be used, for example. Accordingly, the sealing element 234 can also be configured in various ways. As has been described above, one or more sealing lips can be used as an alternative to or in addition to the spring-mounted sealing slide shown in FIG. 2. Such sealing elements can be produced, for example, by means of multi-component injection molding and/or by encapsulation of suitable sealing elements (for example, rubber lips) in a suitable injection molding tool. The sealing element or sealing elements can be opened (alternatively or cumulatively) either by the patient (e.g., via manual slides, etc.) or automatically by a dedicated drive mechanism.

Moreover, the moisture-proof housing 212 in the illustrative embodiment according to FIG. 2 has a pressure-equalizing structure 240. In this illustrative embodiment, this pressure-equalizing structure 240 is designed as a pressure-equalizing membrane 242 which is integrated into the moisture-proof housing 212 (again by encapsulation, for example). This pressure-equalizing membrane 242 prevents penetration of air moisture into the internal atmosphere 214 of the housing and permits pressure equalization between the internal atmosphere 214 of the housing and the external atmosphere 244. This prevents "breathing" of the portable measuring system 210 during which, for example as a result of temperature fluctuations, air exchange could take place through the application opening 232.

The moisture-proof housing 212 as a whole can be designed in such a way that air moisture is kept away from the internal atmosphere 214 of the housing. The moisture-proof housing 212 can also provide protection against entry of splash water or even ensure that the whole portable measuring system 210 is waterproof. This also allows the portable measuring system 210 to be cleaned with aggressive cleaning agents. The moisture introduced into the internal atmosphere 214 of the housing by application of the liquid sample via the application opening 232 can generally be absorbed without any problem by the desiccant 118.

Figure 3:
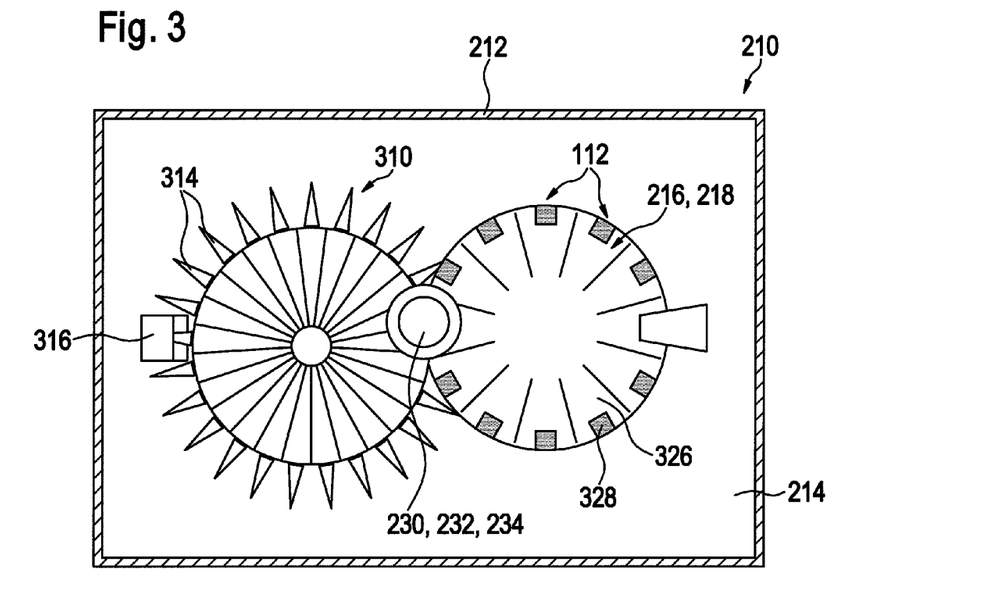
FIG. 3 shows a fully integrated portable measuring system according to the present invention in a sectional plan view.

Instead of the test element support 216 with the drum-shaped retaining structure 218 shown by way of example in FIG. 2, other structures can also be easily used, for example, arrangements in the form of stacks, disks, rows and or zig-zags. FIGS. 2 and 3 show a further example in which the test element support 216 is designed with a circular disk shape in the form of a test strip wheel.

The portable measuring system 210 according to the illustrative embodiment in FIGS. 2 and 3 also contains an integrated lancet system 310 in the form of a multi-tipped lancet wheel mounted so as to be rotated by a drive 312.

During operation, a lancet 314 to be used is first rotated to a kinking station 316. In this kinking station 316, the lancet 314 to be used is kinked upward by 90° (in FIG. 3) by means of a spring mechanism 318. Thereafter, the lancet wheel is rotated through 180° by means of the drive 312, until the upwardly kinked lancet is below the application opening 232 in the housing 212. In this illustrative embodiment, the application opening 232 is designed as a cone and is again closed by a sealing element 234. The sealing element 234 can be pushed aside by the finger 320 of the patient, thus exposing the application opening 232. At the same time, the finger 320 closes this application opening 232. By pressing the finger 320 onto the application opening 232, the skin of the finger 320 in the area of the application opening 232 forms a bulge curving into the interior of the housing 212. When the portable measuring system 210 is triggered, a lancet spring mechanism 322 ensures that the lancet 314, which is located below the application opening 232 and is bent upward, is accelerated and perforates the skin of the finger 320 within the application opening 232. A blood droplet 324 is thus formed.

Figure 4:
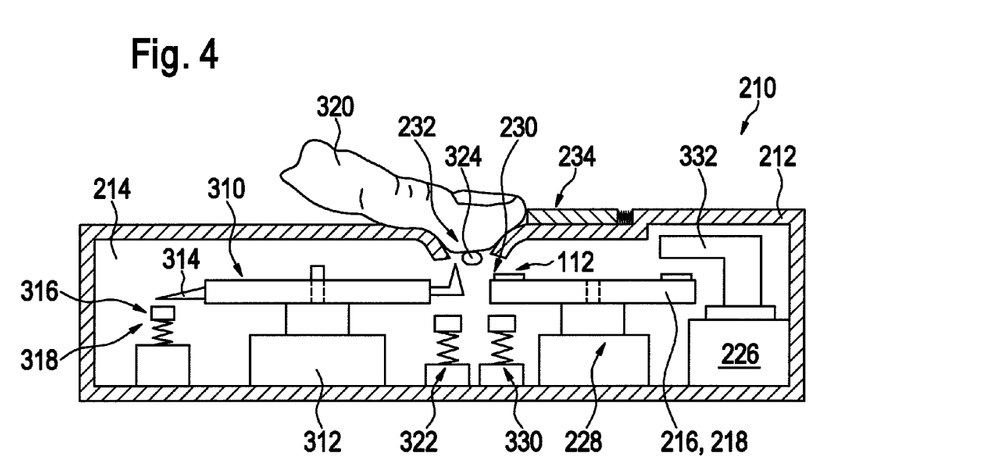
FIG. 4 shows the portable measuring system according to the invention from FIG. 3 in a sectional side view.

The test element support 216 designed in this illustrative embodiment according to FIGS. 3 and 4 as a circular disk is divided into circular disk sectors 326. Each of these circular disk sectors 326 forms a test element 112. Each of these test elements 112 has a reagent layer 328 which, as has been described above, reacts to the presence and/or concentration of the analyte in the liquid sample (blood droplet 324). In this illustrative embodiment according to FIGS. 3 and 4, this reagent layer 328 is, for example, a reagent layer 328 for a color reaction in the presence of glucose, i.e., a reagent layer 328 which, by reaction with glucose, changes its color and/or its fluorescence properties.

After the skin in the area of the application opening 232 has been perforated, a test element spring mechanism 330 briefly bends the test element support 216 upward in the area of the application position below the application opening 232, even as far as the application opening 232. In this way, the blood droplet 324 is applied to the reagent layer 328 of the test element 112 located in the application position 230, and the described reaction can take place.

The release mechanism 228 then turns the test element support 216 through 180° such that the test element 112 on which the blood droplet 324 has been applied is placed above or below an optical reader 332. This optical reader 332 carries out a simple optical measurement, for example, or a measurement of fluorescence excitation. The optical reader 332 is connected to the electronic evaluation device 226, which can be designed analogously to FIG. 2 and can, for example, comprise a microprocessor, operating elements, displays, data memories or the like.

The fully integrated portable measuring system 210 according to the illustrative embodiment in FIGS. 3 and 4 shows particularly clearly the advantages of these teachings. That is, the reagent layer 328 is exposed directly to the internal atmosphere 214 of the housing. A separate sealing of the individual test elements 112 is neither necessary nor desirable. If a seal first had to be removed from the individual reagent layers 328, this would require additional mechanical outlay, which in turn would be disadvantageous in terms of the energy requirement and the assembly space, since further mechanical devices and actuating elements would be needed. Once again, for example, a desiccant 118 (not shown in FIG. 3 or FIG. 4) can be integrated in the test element support 216 designed here in the form of a circular disk.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMBERS 110 portable measuring system (prior art)
112 test element
114 housing
116 primary packaging
117 dispensing opening
118 desiccant
120 opening 210 portable measuring system
212 moisture-proof housing
214 internal atmosphere of housing
216 test element support
218 retaining structure
220 insertion opening
222 receiving seat
224 drive
226 electronic evaluation device
228 release mechanism
230 application position
232 application opening
234 sealing element
236 moisture sensor
238 warning system
240 pressure-equalizing structure
242 pressure-equalizing membrane
244 external atmosphere
310 integrated lancet system
312 drive
314 lancet
316 kinking station
318 spring mechanism
320 finger
322 spring mechanism for lancets
324 blood droplet
326 sectors of circular disk
328 reagent layer
330 spring mechanism for test element
332 optical reader

What is claimed is:

1. A portable measuring system used for analyzing a liquid sample for at least one analyte contained therein, comprising:
a substantially moisture-proof housing having an internal atmosphere, the housing substantially preventing moisture from penetrating into the internal atmosphere;
a test element support that is insertable into the internal atmosphere, the test element support having a retaining structure and a plurality of test elements supported by the retaining structure, the test element support configured such that, after insertion into the internal atmosphere, the test elements are all exposed to the same internal atmosphere;
an application opening through which liquid sample is applied to a test element defined in the housing and having a sealing element disposed proximate the application opening, the sealing element comprising a sealing lip, a sealing ring, a sealing slide, an application flap, a movable sealing element, or a two-component plastic structure with at least one rigid and at least one flexible housing component; and
wherein, the liquid sample is applied through the application opening to the test elements within the internal atmosphere and the sealing element seals the application opening before and after the application of liquid sample.

2. The portable measuring system of claim 1, further comprising a release mechanism configured to convey the test elements into an application position within the internal atmosphere, wherein test elements positioned in the application position are accessible to the liquid sample.

3. The portable measuring system of claim 1, further comprising a desiccant in the internal atmosphere of the housing.

4. The portable measuring system of claim 1, further comprising a pressure-equalizer for substantially preventing penetration of moisture when a pressure of the internal atmosphere changes relative to the air pressure outside the internal atmosphere.

5. The portable measuring system of claim 1, further comprising a flexible volume-modifying element.

6. The portable measuring system of claim 5, wherein the flexible volume-modifying element comprises a pressure-equalizing membrane.

7. The portable measuring system of claim 1, further comprising a moisture sensor or temperature sensor for measuring the moisture or temperature of the internal atmosphere.

8. The portable measuring system of claim 7, further comprising a warning system for emitting a warning to a user if at least one of the following values exceeds one or more pre-defined threshold values: the moisture of the internal atmosphere; the temperature of the internal atmosphere of the housing.

9. The portable measuring system of claim 8, further comprising a climate integrator that takes account of time, moisture and temperature.

10. The portable measuring system of claim 1, wherein the retaining structure has a retaining rotor or drum that is rotatable in the housing.

11. The portable measuring system of claim 1, further comprising a desiccant connected to the test element support.

12. The portable measuring system of claim 1, further comprising an electronic evaluation device for determining the presence or the concentration of the at least one analyte.

13. The portable measuring system of claim 1, further comprising an integrated lancet system for perforating an area of skin.

14. The portable measuring system of claim 13, wherein the integrated lancet system is received in the housing.

15. The portable measuring system of claim 13, wherein the integrated lancet system has a plurality of disposable lancets.

16. The portable measuring system of claim 1, wherein the test elements have a reagent layer which changes at least one property thereof upon contact with the analyte to be detected, further wherein, when the test element support is inserted into the internal atmosphere, the reagent layer of each test element is exposed to the internal atmosphere.

17. A portable measuring system for analyzing a liquid sample for at least one analyte contained therein, comprising:
a substantially moisture-proof housing having an internal atmosphere, the housing having an application opening through which liquid sample is applied to a test element, an openable sealing element disposed proximate the application opening;
a test element support that is removably insertable into the housing, the test element support having a retaining structure and a plurality of test elements supported by the retaining structure, the test elements being exposed to the same internal atmosphere when the test element support is positioned in the housing; and
a release mechanism which conveys the test elements into an application position within the housing, the application position being located near the application opening, wherein test elements positioned in the application position are accessible to the liquid sample and the liquid sample is applied through the application opening to the test elements within the housing, wherein the sealing element seals the application opening before and after the application of liquid sample.

18. The portable measuring system of claim 17, wherein the openable sealing element comprises a sealing lip, a sealing ring, a sealing slide, an application flap, a movable sealing element, or a two-component plastic structure with at least one rigid and at least one flexible housing component.

19. The portable measuring system of claim 17, further comprising a desiccant disposed in the housing.

20. The portable measuring system of claim 17, further comprising a pressure-equalizer for substantially preventing penetration of moisture when a pressure of the internal atmosphere changes relative to the air pressure outside the internal atmosphere.

21. The portable measuring system of claim 17, further comprising a pressure-equalizing membrane.

22. The portable measuring system of claim 1, further comprising a moisture sensor or temperature sensor for measuring the moisture or temperature of the internal atmosphere, and a warning system for emitting a warning to a user if the moisture of the internal atmosphere or the temperature of the internal atmosphere of the housing exceeds a predetermined threshold value.

23. The portable measuring system of claim 17, wherein the retaining structure comprises a rotatable rotor or drum.

* * * * *